United States Patent [19]

Draber et al.

[11] Patent Number: 5,069,712

[45] Date of Patent: Dec. 3, 1991

[54] IMIDAZOLIDINE DERIVATIVES

[75] Inventors: Wilfried Draber; Peter Babczinsky, both of Wuppertal; Hans-Joachim Santel, Leverkusen; Klaus Lürssen; Robert R. Schmidt, both of Bergisch Gladbach, all of Fed. Rep. of Germany

[73] Assignee: Bayer Aktiengesellschaft, Leverkusen, Fed. Rep. of Germany

[21] Appl. No.: 680,212

[22] Filed: Apr. 4, 1991

[30] Foreign Application Priority Data

Apr. 12, 1990 [DE] Fed. Rep. of Germany ....... 4011870

[51] Int. Cl.$^5$ .......................................... A01N 43/50
[52] U.S. Cl. .......................................... 71/92; 548/315
[58] Field of Search ............................ 548/315; 71/92

Primary Examiner—Mary C. Lee
Assistant Examiner—Peter Davis
Attorney, Agent, or Firm—Sprung Horn Kramer & Woods

[57] ABSTRACT

Imidazolidine derivatives of the formula

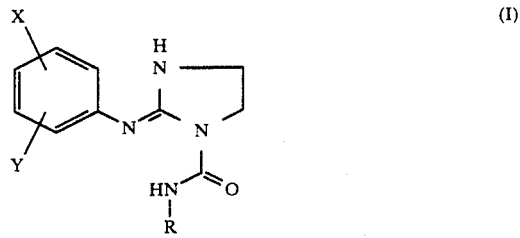

in which
R represents in each case optionally substituted alkyl, cycloalkyl or aryl and
X and Y independently of one another represent hydrogen, halogen, cyano, nitro or carboxyl, or represent in each case optionally substituted alkyl, alkoxy, alkoxycarbonyl, alkylthio, alkylsulphinyl or alkylsulphonyl, are useful as herbicides. A process for preparing the imidazolidine derivatives is also disclosed.

11 Claims, No Drawings

IMIDAZOLIDINE DERIVATIVES

The invention relates to new imidazolidine derivatives, to a process for their preparation, and to their use as herbicides.

New imidazolidine derivatives of the general formula (I)

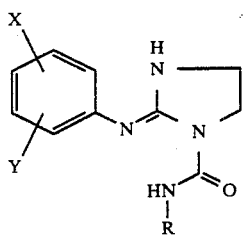

in which
R represents in each case optionally substituted alkyl, cycloalkyl or aryl and
X and Y independently of one another represent hydrogen, halogen, cyano, nitro or carboxyl, or represent in each case optionally substituted alkyl, alkoxy, alkoxycarbonyl, alkylthio, alkylsulphinyl or alkylsulphonyl,
have been found.

Furthermore, it has been found that the new imidazolidine derivatives of the formula (I) are obtained when imidazolidines of the general formula (II)

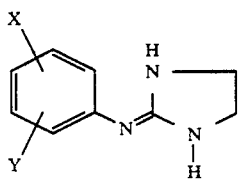

in which
X and Y have the abovementioned meaning,
and/or tautomers of the imidazolidines of the formula (II),
are reacted with isocyanates of the general formula (III)

R—N=C=O                    (III)

in which
R has the abovementioned meaning,
if appropriate in the presence of a diluent.

Finally, it has been found that the new imidazolidine derivatives of the formula (I) have interesting herbicidal properties.

Formula (I) provides a general definition of the imidazolidine derivatives according to the invention. In formula (I),
R preferably represents straight-chain or branched alkyl having 1 to 6, preferably 1 to 4, carbon atoms which is optionally substituted by halogen, or represents cycloalkyl having 3 to 8, preferably 3 to 6, carbon atoms which is optionally substituted by straight-chain or branched alkyl having 1 to 4 carbon atoms, in particular methyl or ethyl, or represents phenyl which is optionally substituted by cyano, nitro or halogen, or represents alkyl, alkoxy or alkylthio, each of which has 1 to 4 carbon atoms and each of which is optionally substituted by halogen, and
X and Y independently of one another preferably represent hydrogen, halogen, cyano, nitro or carboxyl, or represent alkyl, alkoxy, alkoxycarbonyl, alkylthio, alkylsulphinyl or alkylsulphonyl, each of which has up to 4 carbon atoms and each of which is optionally substituted by halogen.

Particularly preferred compounds of the formula (I) are those in which
R represents methyl, ethyl, propyl, isopropyl, butyl, isobutyl, sec-butyl, tert-butyl, chloro-tert-butyl, fluoro-tert-butyl, cyclopentyl, methyl-cyclopentyl, ethyl-cyclopentyl, cyclohexyl, methyl-cyclohexyl, ethyl-cyclohexyl or represents phenyl which is optionally mono-, di- or trisubstituted by identical or different substituents from the series comprising cyano, nitro, fluorine, chlorine, bromine, methyl, ethyl, difluoromethyl, chlorodifluoromethyl, trifluoromethyl, methoxy, ethoxy, difluoromethoxy, chlorodifluoromethoxy, trifluoromethoxy, methylthio, ethylthio, difluoromethylthio, chlorodifluoromethylthio or trifluoromethylthio, and
X and Y independently of one another represent hydrogen, fluorine, chlorine, bromine, cyano, nitro, carboxyl, methyl, ethyl, difluoromethyl, chlorodifluoromethyl, trifluoromethyl, methoxy, ethoxy, propoxy, isopropoxy, difluoromethoxy, chlorodifluoromethoxy, trifluoromethoxy, methoxycarbonyl, ethoxycarbonyl, propoxycarbonyl, isopropoxycarbonyl, methylthio, ethylthio, difluoromethylthio, trifluoromethylthio, chlorodifluoromethylthio, methylsulphinyl, ethylsulphinyl, trifluoromethylsulphinyl, chlorodifluoromethylsulphinyl, trifluoromethylsulphonyl or chlorodifluoromethylsulphonyl, where X is, in particular, in the 3-phenyl position.
R represents, in particular, mono- or disubstituted phenyl, the substituents selected being nitro, fluorine, chlorine, methyl, ethyl, n- or iso-propyl, trifluoromethyl, trifluoromethoxy or trifluoromethylthio.
X represents, in particular, hydrogen, trifluoromethyl, methyl, methoxy, ethoxy, propoxy or isopropoxy, it being preferred for the substituents to be in the 3-phenyl position.
Y represents, in particular, hydrogen.

Examples of the compounds of the formula (I) are listed in Table 1 below.

TABLE 1

Examples of the compounds of the formula (I)

| R | (Position-)X | (Position-)Y |
|---|---|---|
| —CH(CH₃)C₂H₅ | (3-)Cl | H |
| 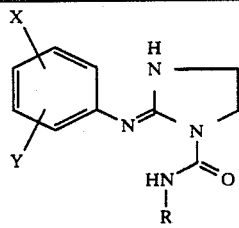 | (2-)F | (4-)Cl |

TABLE 1-continued

Examples of the compounds of the formula (I)

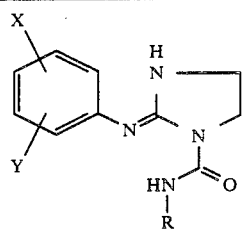

(I)

| R | (Position-)X | (Position-)Y |
|---|---|---|
| $C_2H_5$ | (3-)Cl | (5-)Cl |
| 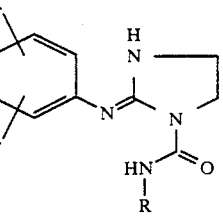 —F | (3-)CF$_3$ | H |
| 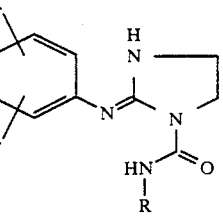 —CH$_3$ (4-position F) | (4-)F | H |
| 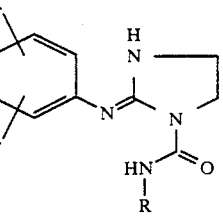 —F | (3-)OCF$_3$ | H |
| 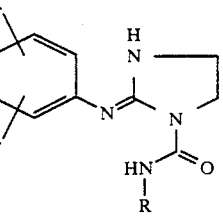 —Cl | (3-)CF$_3$ | H |
| 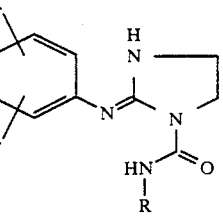 —Cl, Cl | (3-)O—CH(CH$_3$)$_2$ | H |
| 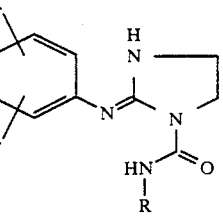 —Cl | (3-)OCH(CH$_3$)$_2$ | H |
| 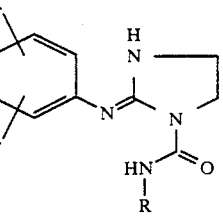 —F, F | (3-)OCH$_3$ | H |
| 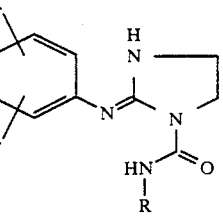 —F | (4-)CO$_2$CH$_3$ | H |
| 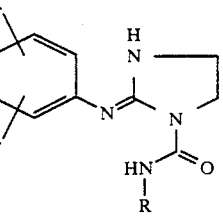 —Cl | (3-)CO$_2$CH(CH$_3$)$_2$ | H |
| 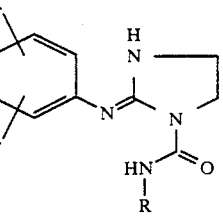 —OCH$_3$ | (3-)F | (4-)Cl |

If, for example, 2-(3-cyano-phenyl-imino)-imidazolidine and 2-fluorophenyl isocyanate are used as starting substances for the process according to the invention for the preparation of the compounds of the formula (I), the course of the reaction can be represented by the following equation:

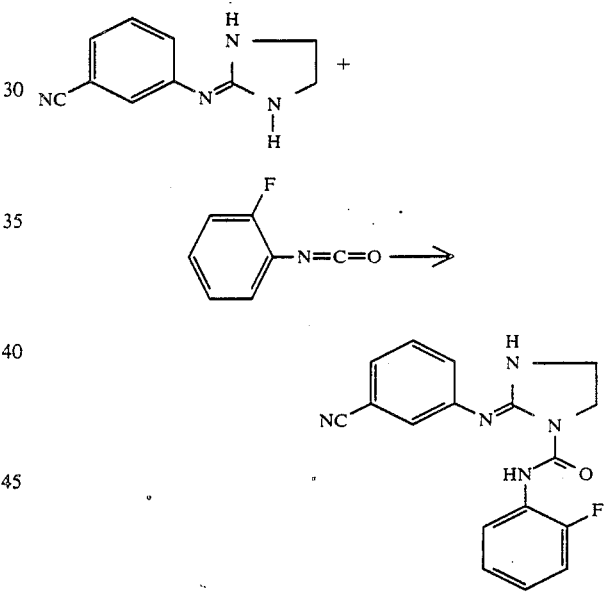

Formula (II) provides a general definition of the imidazolidines to be used as starting substances in the process according to the invention for the preparation of compounds of the formula (I).

In formula (II), X and Y preferably, or in particular, have those meanings which have already been mentioned above in connection with the description of the compounds of the formula (I) according to the invention as being preferred, or particularly preferred, for X and Y.

The starting substances of the formula (II)—or their tautomers—are known and/or can be prepared by processes known per se (cf. J. Org. Chem. 24 (1959), 884; J. Het. Chem. 11 (1974), 257–262; German Patent 1,303,930; British Patent 1,382,752).

For example, the imidazolidines of the formula (II) are obtained when 2-chloro-imidazoline of the formula (IV)

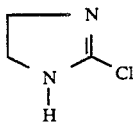

or salts thereof are reacted with arylamines of the general formula (V)

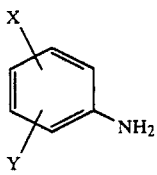

in which

X and Y have the abovementioned meaning,
in the presence of an acid-binding agent such as, for example, sodium hydroxide, and in the presence of a diluent such as, for example, methylene chloride, at temperatures between 0° C. and 100° C.

2-Chloro-imidazoline and the salts thereof are known (cf. J. Het. Chem. 11 (1974), 257–262).

The arylamines of the formula (V) are likewise known chemicals for synthesis.

Formula (III) provides a general definition of the isocyanates furthermore to be used as starting substances in the process according to the invention for the preparation of compounds of the formula (I).

In formula (III), R preferably, or in particular, has the meaning which has already been mentioned above in connection with the description of the compounds of the formula (I) according to the invention as being preferred, or particularly preferred, for R.

The starting substances of the formula (III) are known chemicals for organic synthesis, or they can be prepared by known processes.

The process according to the invention for the preparation of the new imidazolidine derivatives of the formula (I) is preferably carried out using diluents. Diluents which are suitable for this purpose are practically all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether, dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone, and also dimethyl sulphoxide, tetramethylene sulphone and hexamethylphosphoric triamide.

When carrying out the process according to the invention, the reaction temperatures can be varied within a substantial range. In general, the process is carried out at temperatures between −20° C. and +150° C., preferably at temperatures between 0° C. and 100° C.

The process according to the invention is generally carried out under atmospheric pressure. However, it is also possible for the process to be carried out under increased or reduced pressure.

For carrying out the process according to the invention, the starting substances required in each case are generally employed in approximately equimolar amounts. However, it is also possible to use one of the two components employed in each case in a relatively large excess. In general, the reactions are carried out in a suitable diluent, and the reaction mixture is stirred for several hours at the particular temperature required. Working-up in the process according to the invention is carried out in each case by customary methods (cf. the Preparation Examples).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pastureland and for the selective combating of weeds in annual cultures.

The compounds of the formula (I) according to the invention are suitable, for example, for selectively combating monocotyledon and dicotyledon weeds in dicotyledon crops such as soya or sunflowers.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable components for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethyl-urea (METABENZTHIAZURON) for combating weeds in cereals; 4-amino-3-nethyl-6-phenyl-1,2,4-triazin-5(4H)-one (METAMITRON) for combating weeds in sugar beet and 4-amino-(6-1,1-dimethylethyl)-3-methylthio-1,2,4-triazin-5(4H)-one (METRIBUZIN) for combating weeds in soya beans; furthermore also N-(methoxymethyl)-2,6-diethylchloroacetanilide (ALACHLOR); ethyl-2-([(4-chloro-6-methoxy-2-pyrimidinyl)-aminocarbonyl]-aminosulphonyl}-benzoate (CHLORIMURON); exo-1-methyl-4-(1-methylethyl)-2-(2-methyloxy)-7-oxabicyclo-(2,2,1)-heptane (CINMETHYLIN); 2-[(2-chlorophenyl)-methyl]-4,4-dimethylisoxazolidin-3-one (DIMETHAZONE); 4-amino-6-t-butyl-3-ethylthio-1,2,4-triazin-5(4H)-one (ETHIOZIN); 2-[5-methyl-5-(1-methylethyl)-4-oxo-2-imidazolin-2-yl]-3-quinolinecarboxylic acid (IMAZAQUIN); 2-[4,5-dihyiro-4-methyl-4-isopropyl-5-oxo-(1H)-imidazol-2-yl]-5-ethyl-pyridine-3-carboxylic acid (IMAZETHAPYR); N-methyl-2-(1,3-benzothiazol-2-yloxy)-acetanilide(MEFENACET);2-chloro-N-(2,6-dimethylphenyl)-N-[(1H)-pyrazol-1-yl-methyl]-acetamide (METAZACHLOR); 2-ethyl-6-methyl-N-(1-methyl-2-methoxyethyl)-chloroacetanilide (METOLACHLOR); methyl 3-[[[[(4-methoxy-6-methyl-1,3,5-triazin-2-yl)-amino]-carbonyl]-amino]-sulphonyl]-thiophene-2-carboxylate (THIAMETURON); 2,6-dinitro-4-trifluoromethyl-N,N-dipropylaniline (TRIFLURALIN). Surprisingly, some mixtures also show synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1

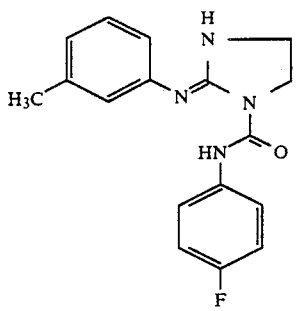

A solution of 13.7 g (0.1 mol) of 4-fluoro-phenyl isocyanate in 25 ml of methylene chloride is added dropwise to a solution of 17.5 g (0.1 mol) of 2-(3-methyl-phenylimino)-imidazolidine in 250 ml of methylene chloride, with ice-cooling and stirring. After the ice bath has been removed, the reaction mixture is stirred for 3 hours at 10° C. to 20° C. and subsequently filtered. The filtrate is dried with sodium sulphate and concentrated, the residue is stirred with diethyl ether, and the crystalline product is isolated by filtration with suction and recrystallized from ethyl acetate.

25.0 g (80% of theory) of 1-(4-fluoro-phenyl-aminocarbonyl)-2-(3-methyl-phenylimino)-imidazolidine of melting point 178° C. are obtained.

The compounds of the formula (I) listed in Table 2 below can, for example, also be prepared analogously to Example 1 and in accordance with the general description of the preparation process according to the invention.

TABLE 2
Examples of the compounds of the formula (I)

| Ex. No. | R | (Position-)X | (Position-)Y | Melting point (°C.) |
|---|---|---|---|---|
| 2 | 3-CF$_3$-phenyl | H | H | 138 |
| 3 | 3-CH$_3$-phenyl | H | H | 189 |
| 4 | 3,5-dichlorophenyl | (3-)CF$_3$ | H | 150 |
| 5 | 4-chlorophenyl | (3-)CF$_3$ | H | 166 |
| 6 | 3,5-dichlorophenyl | (3-)CH$_3$ | H | 181 |
| 7 | 4-chlorophenyl | (3-)CH$_3$ | H | 188 |

TABLE 2-continued

Examples of the compounds of the formula (I)

(I)

| Ex. No. | R | (Position-)X | (Position-)Y | Melting point (°C.) |
|---|---|---|---|---|
| 8 | 2,4-difluorophenyl | (3-)CH$_3$ | H | 175 |
| 9 | 2,4-difluorophenyl | (3-)CF$_3$ | H | 198 |
| 10 | 4-fluorophenyl | (3-)CF$_3$ | H | 180 |
| 11 | 4-chlorophenyl | (3-)OCH$_3$ | H | 163 |
| 12 | 3,4-dichlorophenyl | (3-)OCH$_3$ | H | 160 |
| 13 | 4-fluorophenyl | (3-)OCH$_3$ | H | 156 |
| 14 | 4-fluorophenyl | (3-)OCH(CH$_3$)$_2$ | H | 157 |
| 15 | 4-chlorophenyl | (3-)OCH(CH$_3$)$_2$ | H | 165 |
| 16 | phenyl | (3-)OCH(CH$_3$)$_2$ | H | 148 |
| 17 | 4-OCF$_3$-phenyl | (3-)OCH(CH$_3$)$_2$ | H | 177 |

TABLE 2-continued
Examples of the compounds of the formula (I)
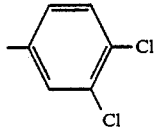
(I)
| Ex. No. | R | (Position-)X | (Position-)Y | Melting point (°C.) |
|---|---|---|---|---|
| 18 | 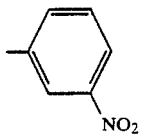 | (3-)OCH(CH₃)₂ | H | 122 |
| 19 | 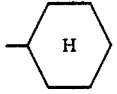 | (3-)OCH(CH₃)₂ | H | 123 |
| 20 | 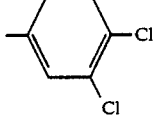 | (3-)OCH(CH₃)₂ | H | 164 |
| 21 | 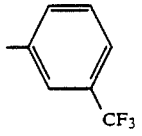 | (3-)OCH₃ | H | 167 |
| 22 | 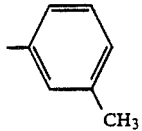 | (3-)OCH(CH₃)₂ | H | 115 |
| 23 |  | (3-)OCH(CH₃)₂ | H | 111 |
| 24 | 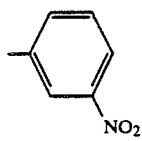 | (3-)OCH(CH₃)₂ | H | 175 |
| 25 | 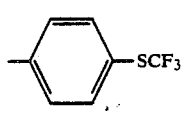 | (3-)CH₃ | H | 165 |
| 26 |  | (3-)OCH(CH₃)₂ | H | 164 |

TABLE 2-continued
Examples of the compounds of the formula (I)

(I)

| Ex. No. | R | (Position-)X | (Position-)Y | Melting point (°C.) |
|---|---|---|---|---|
| 27 | —⟨phenyl⟩—SCF₃ | (3-)OCH₃ | H | 135 |
| 28 | —⟨phenyl⟩—SCF₃ | (3-)CF₃ | H | 152 |

STARTING SUBSTANCES OF THE FORMULA (II)

Example (II-1)

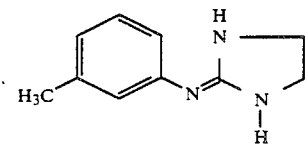

A solution of 60 g (1.5 mol) of sodium hydroxide in 300 ml of water is added dropwise at 20° C. to a mixture of 94.2 g (0.5 mol) of 2-chloro-imidazoline sulphate, 53.5 g of 3-methyl-aniline and 1 liter of methylene chloride, and the reaction mixture is stirred for 20 hours at 20° C. The organic phase is subsequently separated off, dried with sodium sulphate and filtered. The filtrate is concentrated, the residue is crystallized by trituration with diethyl ether, and the crystalline product is isolated by filtration with suction.

34 g (39% of theory) of 2-(3-methyl-phenylimino)imidazolidine of melting point 115° C. are obtained.

The compounds of the formula (II) listed in Table 3 below can, for example, also be prepared analogously to Example (II-1).

TABLE 3
Examples of the starting substances of the formula (II)

(II)

| Ex. No. | X | Y | Melting point (°C.) |
|---|---|---|---|
| II-2 | (3-)CF₃ | H | 93 |
| II-3 | (3-)OCH₃ | H | 97 |

TABLE 3-continued
Examples of the starting substances of the formula (II)

(II)

| Ex. No. | X | Y | Melting point (°C.) |
|---|---|---|---|
| II-4 | (3-)OCF₃ | H | 102 |

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a powerful action against weeds is shown, for example, by the compounds of Preparation Examples 8, 9, 10 and 13, which are also well tolerated by crop plants such as, for example, soya and sunflowers.

What is claimed is:

1. An imidazolidine derivative of the formula (I) in which

R represents straight-chain or branched alkyl having 1 to 6 carbon atoms which is optionally substituted by halogen, or represents cycloalkyl having 3 to 8 carbon atoms which is optionally substituted by straight-chain or branched alkyl having 1 to 4 carbon atoms, or represents phenyl which is optionally substituted by cyano, nitro or halogen, or represents alkyl, alkoxy or alkylthio, each of which has 1 to 4 carbon atoms and each of which is optionally substituted by halogen, and X and Y independently of one another represents hydrogen, halogen, cyano, nitro or carboxyl, or represents alkly, alkoxy, alkoxycarbonyl, alkylthio, alkylsulphinyl or alkylsulphonyl, each of which has up to 4 carbon atoms and each of which is optionally substituted by halogen.

2. An imidazolidine derivative of the formula (I) according to claim 1, in which R represents methyl, ethyl, propyl, isopropyl, butyl, isobutyl, sec-butyl, tert-butyl, chloro-tert-butyl, fluoro-tert-butyl, cyclopentyl, methyl-cyclopentyl, ethyl-cyclopentyl, cyclohexyl, methyl-cyclohexyl, ethyl-cyclohexyl, or represents phenyl which is optionally mono-, di- or trisubstituted by identical or different substituents selected from the group consisting of cyano, nitro, fluorine, chlorine, bromine, methyl, ethyl, difluoromethyl, chlorodifluoromethyl, trifluoromethyl, methoxy, ethoxy, difluoromethoxy, chlorodifluoromethoxy, trifluoromethoxy, methylthio, ethylthio, difluoromethylthio, chlorodifluoromethylthio or trifluoromethylthio, and X and Y independently of one another represent hydrogen, fluorine, chlorine, bromine, cyano, nitro, carboxyl, methyl, ethyl, difluoromethyl, chlorodifluoromethyl, trifluoromethyl, methoxy, ethoxy, propoxy, isopropoxy, difluoromethoxy, chlorodifluoromethoxy, trifluoromethoxy, methoxycarbonyl, ethoxycarbonyl, propoxycarbonyl, isopropoxycarbonyl, methylthio, ethylthio, difluoromethylthio, trifluoromethylthio, chlorodifluoromethylthio, methylsulphinyl, ethylsulphinyl, trifluoromethylsulphinyl, chlorodifluoromethylsulphinyl, trifluoromethylsulphonyl or chlorodifluoromethylsulphonyl.

3. An imidazolidine derivative of the formula (I) according to claim 1, in which R represents mono- or disubstituted phenyl, the substituents being selected from the group consisting of fluorine, chlorine, methyl, ethyl, n- or iso-propyl or trifluoromethyl.

4. An imidazolidine derivative according to claim 1, having the formula

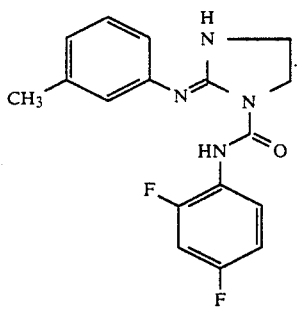

5. An imidazolidine derivative according to claim 1, having the formula

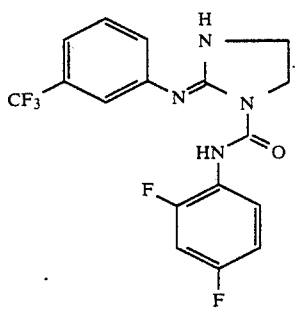

6. An imidazolidine derivative according to claim 1, having the formula

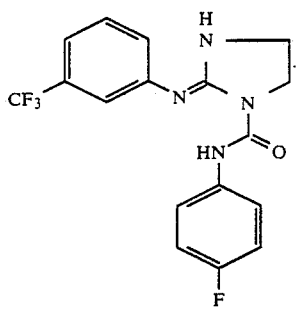

7. An imidazolidine derivative according to claim 1, having the formula

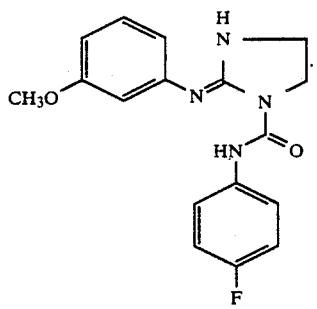

8. A herbicidal composition comprising a herbicidally effective amount of an imidazolidine derivative according to claim 1 and a carrier.

9. A herbicidal composition according to claim 8, wherein the imidazolidine derivative is selected from the group consisting of

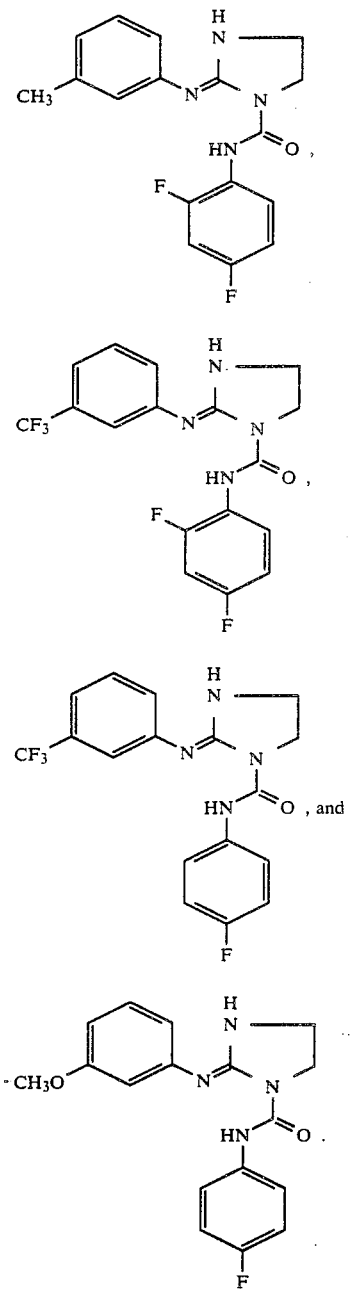

10. A method for combating unwanted vegetation, which comprises applying to such vegetation or to a locus from which it is desired to exclude such vegetation a herbicidally effective amount of an imidazolidine derivative according to claim 1.

11. A method according to claim 10 wherein the imidazolidine derivative is selected from the group consisting of

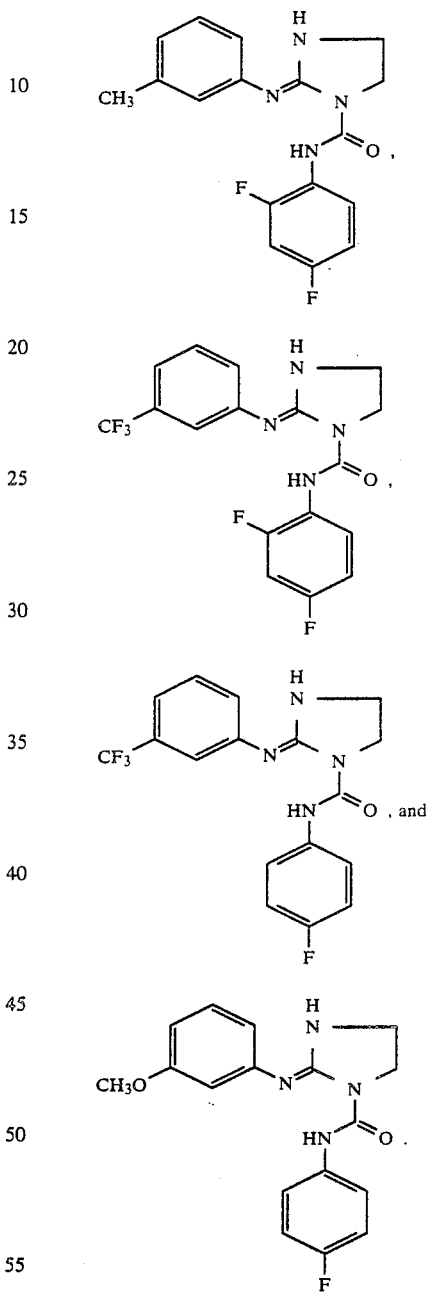

* * * * *